(12) United States Patent
Bartsch

(10) Patent No.: US 8,323,957 B2
(45) Date of Patent: Dec. 4, 2012

(54) DEVICE AND METHOD FOR THE INCUBATION OF CELLS

(75) Inventor: Olaf Bartsch, Hamburg (DE)

(73) Assignee: Eppendorf AG, Hamburg (DE)

( * ) Notice: Subject to any disclaimer, the term of this patent is extended or adjusted under 35 U.S.C. 154(b) by 886 days.

(21) Appl. No.: 12/162,436

(22) PCT Filed: Nov. 17, 2006

(86) PCT No.: PCT/EP2006/011032
§ 371 (c)(1),
(2), (4) Date: Feb. 5, 2009

(87) PCT Pub. No.: WO2007/085284
PCT Pub. Date: Aug. 2, 2007

(65) Prior Publication Data
US 2009/0155885 A1    Jun. 18, 2009

(30) Foreign Application Priority Data
Jan. 30, 2006    (DE) .......... 10 2006 004 157

(51) Int. Cl.
*C12M 3/00*    (2006.01)
(52) U.S. Cl. ............................. 435/288.4; 435/325

(58) Field of Classification Search .............. None
See application file for complete search history.

(56) References Cited

U.S. PATENT DOCUMENTS

| | | |
|---|---|---|
| 3,562,114 A | 2/1971 | Steidl et al. |
| 6,500,666 B1 | 12/2002 | Clements-Macak et al. |
| 6,518,059 B1 | 2/2003 | Butts |
| 7,270,996 B2 * | 9/2007 | Cannon et al. ............ 435/293.1 |
| 2011/0129923 A1 * | 6/2011 | Wilson et al. ................ 435/395 |

FOREIGN PATENT DOCUMENTS

| | | |
|---|---|---|
| DE | 3924701 | 1/1991 |
| DE | 19536373 | 12/1996 |
| JP | 10262646 | 10/1998 |
| JP | 2004154099 | 6/2004 |
| JP | 2005143474 | 6/2005 |
| WO | 0077164 | 12/2000 |

* cited by examiner

*Primary Examiner* — James Martinell
(74) *Attorney, Agent, or Firm* — Vidas, Arrett & Steinkraus, P.A.

(57) ABSTRACT

Device for the incubation of cells comprising a sterile or sterilizable, portable receptacle for enclosing in a contamination-proof manner at least one integrated and/or insertable culture vessel for accommodating cells with at least one closable opening for introducing and/or removing cells and/or culture medium and/or a culture vessel into and/or from the receptacle and at least one device for creating culture conditions in the receptacle.

38 Claims, 1 Drawing Sheet

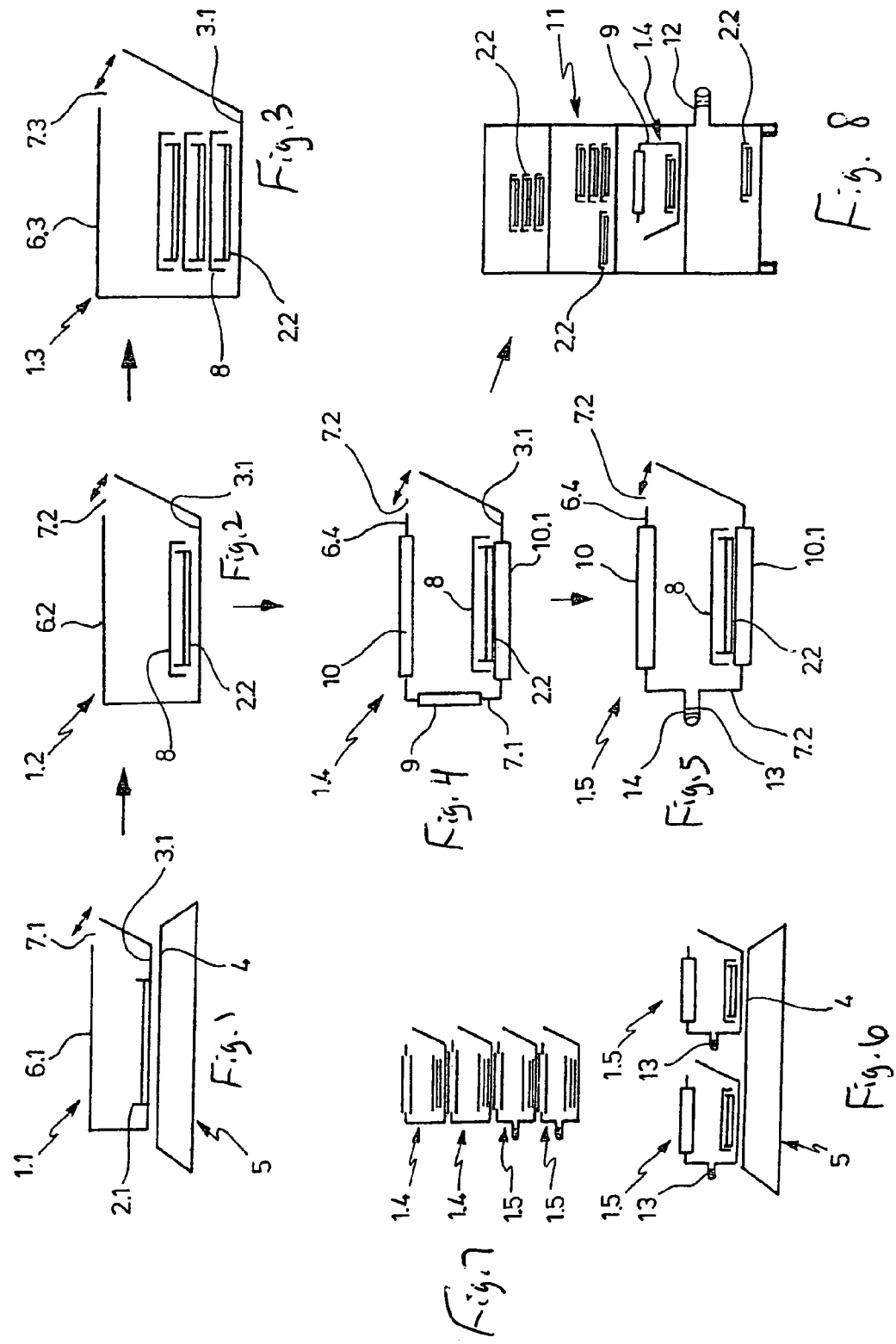

DEVICE AND METHOD FOR THE INCUBATION OF CELLS

CROSS-REFERENCE TO RELATED APPLICATIONS

Not applicable.

STATEMENT REGARDING FEDERALLY SPONSORED RESEARCH

Not applicable.

BACKGROUND OF THE INVENTION

The invention relates to a device and to a method for the incubation of cells.

Conventionally, cells for incubation are filled into a culture vessel and the culture vessel is inserted into an incubator. Optimal conditions for the incubation of cell cultures are provided in the incubator, by an atmosphere and temperature (for example 37°) being set which is suitable therefor. The atmosphere is generally created by air with a specific $CO_2$ and $O_2$ content and a specific air humidity. The culture vessel is, for example, a multiwell culture plate containing a plurality of receivers, a culture flask or a culture dish. The cells are protected by loosely positioning a lid on culture plates and culture dishes. The loosely positioned lid makes it possible for the atmosphere prevailing in the incubator to be applied to the cells on the culture plate and/or the culture dish. Culture flasks have a closure with an integral filter, which also ensures that the atmosphere is applied to the cells.

In the cell culture laboratory, generally a plurality of users share a large incubator. The culture conditions in the incubator may be influenced by different users. Thus it is not excluded that different users alter the culture conditions so that they are optimised for the incubation of their specific cell cultures. Moreover, there is the risk of cross contamination, for example by mycoplasma. By the repeated opening of the doors and introducing new cell material, the users may introduce further contaminants. Moreover, they may place the culture vessels of other users in a different position, and as a result, make it difficult to find them again and/or mix them up.

Proceeding therefrom, the object of the invention is to provide a device and a method for the incubation of cells, which promotes the maintenance of the desired culture conditions during the incubation of cell cultures.

BRIEF SUMMARY OF THE INVENTION

The device according to the invention for the incubation of cells comprises a sterile or sterilisable, portable receptacle for enclosing in a contamination-proof manner at least one integrated and/or insertable culture vessel for accommodating cells with at least one closable opening for introducing and/or removing cells and/or culture medium and/or a culture vessel into and/or from the receptacle and at least one device for creating culture conditions in the receptacle.

In the method according to the invention for the incubation, at least one culture vessel containing cells is provided enclosed by a sterile, portable receptacle in a contamination-proof manner, and culture conditions are created in the receptacle.

According to the invention, the culture vessels for the incubation are moved into a receptacle and/or are integrated in a receptacle. A multiwell culture plate, culture flask or another culture carrier suitable for the incubation of cell cultures is understood by the term "culture vessel". When the culture vessel is integrated in the receptacle it forms only one part of the receptacle. A culture flask, which is simultaneously a culture vessel and a receptacle closed in a contamination-proof manner, is not a component of the invention. The receptacle seals the specific cell culture in a sterile manner against the environment. The culture conditions are created in the receptacle, such as for example temperature, atmosphere (for example $CO_2$ and $O_2$ and humidity content). The culture conditions are, for example, created in an incubator and introduced into the receptacle. According to a further example, they are created by treating the culture vessel in the receptacle with gas at a defined and possibly tempered atmosphere. The treatment with gas may be undertaken by means of a suitable gassing device. According to a further example, as a result of the heat transmission between a tempering device and the receptacle a specific temperature is generated in the receptacle. The receptacle is, for example, a reusable receptacle which may possibly be sterilised and reused. According to a further example, the receptacle is a single-use item which may be discarded after a single use.

The invention thus allows individual cell culture, screened from undesired interference. As a result, sensitive samples may be separated from one another and incubated in an undisturbed manner. The risk of cross contamination, but also the general risk of contamination is reduced by the isolated incubation. The invention provides advantages for users where space is limited. Incubators may be used more effectively. Incubators have to be carefully cleaned at regular intervals. With contaminated incubators which are difficult to clean, the invention avoids the contamination of the individual cell culture. The user becomes more flexible, as his/her dependency on the infrastructure in the laboratory is reduced. If the available incubators are not adequate for establishing a plurality of different conditions simultaneously, such as for example incubation at 37° C., at 30° C., separate from cell lines and primary cells, the invention offers the possibility of carrying out an incubation under specific culture conditions in the receptacle, even without an incubator, which may be created by treating the receptacle with gas. Moreover, the device also makes possible the incubation of cells outside the cell culture laboratory in a different working environment. As a result of the portability of the receptacle, it is ensured that it may be easily handled by the user and may be positioned in a space-saving manner in the incubator or elsewhere.

The invention may be used for non-biological and biological applications, for example for the incubation of bacteria, fungi, yeasts, higher eukaryotic cells and tissues. The application is particularly recommended when the biological material is either very valuable or very sensitive, for example with primary cell cultures or stem cell cultures.

According to one embodiment, the device comprises at least one culture vessel. This may, for example, be integrated into the receptacle.

According to a further embodiment, the device has at least one culture vessel integrated in the receptacle. The receptacle is thus provided from the outset with a culture vessel. The culture vessel may be contained loosely in the receptacle. According to one embodiment, the culture vessel is connected fixedly and inseparably to the receptacle. The receptacle and culture vessel are, for example, originally produced in one piece or produced separately and combined together in a manner which is fixed and inseparable.

According to one embodiment, devices are present for the releasable connection of at least one culture vessel to the receptacle. To this end, the receptacle and culture vessel have, for example, a clamped, plug or latched connection or a further suitable device for the releasable connection.

According to one embodiment, the receptacle is suitable for enclosing and/or inserting and/or removing at least one culture plate and/or at least one culture flask and/or at least one culture dish. Thus the receptacle has an interior of a shape and size which allow at least one of the aforementioned culture vessels to be enclosed and/or has at least one opening, which is measured and designed such that it allows the insertion and/or the removal of at least one of the aforementioned culture vessels.

The device for creating culture conditions in the receptacle may be designed in different ways.

According to one embodiment, the device for creating culture conditions comprises at least one sterile filter in at least one wall of the receptacle. The sterile filer allows the use of conventional incubators for the passive treatment of the receptacle with gas. The atmosphere prevailing in the incubator may penetrate the receptacle through the sterile filter of the receptacle used, without contaminating the cell culture. It is possible to set a specific temperature in the receptacle by a gas at the specific temperature entering the receptacle through the sterile filter.

The sterile filter partially or entirely occupies, for example, one or more walls of the receptacle, for example, if only one part of one or more walls is designed as a sterile filter. According to a further example, all walls of the receptacle are entirely designed as sterile filters.

The sterile filter is, for example, a porous membrane, as is used in known filter-screw closures for cell culture flasks, suspension culture flasks, and roller bottles. For example, a commercially available capillary pore membrane and usable according to the invention has a pore size of approximately 0.2 μm made of PET/PTFE. In this case, it is the Bio-One-Membrane of the Greiner company (www.gbo.com/bio-science).

A membrane is, for example, able to be sealingly connected, for example by welding at the edge, to a wall of a receptacle made of a suitable plastic which may be welded to the plastic of the membrane. According to a further example, the membrane is extrusion-coated at the edge with the material of the wall. According to a further example, the membrane is sealingly clamped at the edge to the wall of the receptacle, for example by means of a frame covering the edge of the membrane, which is connected to the receptacle via suitable fastening means (for example screws or rivets) or when designed from a suitable plastic is welded on the periphery to the receptacle. Optionally, an additional seal made of resilient material is present between the membrane and the wall of the receptacle. The receptacle is, for example, a rigid or more or less resilient receptacle.

According to a further embodiment, the sterile filter is integrated in at least one wall of the receptacle, i.e. integrally designed with the wall. To this end, for example, a wall is partially or entirely designed from a porous plastic (for example a cellular material). Optionally, the entire receptacle may consist of the porous plastic. The receptacle is, for example, produced in a single or multiple component injection-moulding method from the porous plastic and optionally at least one further plastic. The receptacle is, for example, a rigid or a more or less resilient receptacle.

According to one embodiment, the device for creating culture conditions comprises an incubator with integral tempering device and gassing device for accommodating at least one receptacle. The tempering device controls, for example, the temperature of the gas supplied by the gassing device introduced into the incubator. According to a further example, the tempering device controls the temperature of the depositing surface on which the receptacles are deposited with the culture vessels contained therein.

According to one embodiment, the device for creating culture conditions comprises at least one connection of the receptacle with a through-passage traversing a wall of the receptacle for attaching the receptacle to at least one gassing device. The connection allows the receptacle to be actively treated with gas and optionally tempered by means of external gassing, and possibly tempering, devices. The tempering is carried out, for example, by a tempered gas and/or via a heatable depositing surface of a gassing and tempering device. A gassing, and possibly tempering, device is, for example, designed as a docking station and/or supply station to which at least one portable receptacle may be attached.

According to one embodiment, the device for creating culture conditions comprises a gassing device and at least one tube via which the gassing device is connected or may be connected to at least one connection.

According to one embodiment, the connection comprises a valve for opening and closing the through-passage. When the valve is closed, the device may be used for incubation in a conventional incubator.

According to one embodiment, the device for creating culture conditions comprises at least one open vessel which is integrated in the receptacle and/or which may be inserted into the receptacle for evaporating a liquid introduced into the vessel. A liquid, for example sterile water, may be filled into the vessel which, for example, is designed as a dish or tray so that in the receptacle an atmosphere is created which is saturated with the vapour of the liquid and which prevents the evaporation of culture medium.

According to one embodiment, the device for creating culture conditions comprises a mixing device on which the receptacle is arranged or may be arranged in order to subject the receptacle to a mixing motion.

According to one embodiment, at least one opening of the receptacle is reclosable. The reclosability of the opening makes it possible to use the receptacle after removing a sample and/or after removing and reinserting the culture vessel for the incubation of cell cultures.

The reclosable opening comprises, for example, a cap with a screw closure or bayonet closure or a pivotable flap and optionally a sealing element which, when the cap and/or flap is closed, is effective between said cap and/or flap and the edge of the opening of the receptacle. The screw closure and/or bayonet closure has threads and/or bayonet connecting elements on the cap and on the opening of the receptacle. The sealing element is, for example, a sealing ring or a sealing lip made of a resilient plastic or made of rubber. The sealing element is, for example, configured integrally with the cap, the flap or the receptacle or attached or injection-moulded. The flap is, for example, able to be fixed by, for example, latching or by means of a bar in the closed state to the receptacle.

The receptacle comprises, according to one embodiment, a plurality of different openings, the different openings serving different purposes, for example the introduction and/or removal of cells and/or culture medium and/or other liquids and/or agents.

According to one embodiment, the receptacle comprises at least one optical window for observing the cells in the culture vessel. The optical window has a surface quality which makes it possible to observe the cells in the culture vessel under the microscope. This makes it possible for the user to carry out an analysis of the cell culture by using a microscope. According to one embodiment, the optical window is at a distance from the cell culture vessel which is selected to be so short (for example max 20 mm) such that an analysis of the cells under the microscope is possible.

The receptacle is designed at least in the region of the window from a material with a transparency which is sufficient for microexamination. This is, for example, polystyrol or acryl glass. These materials also have sufficient thermal stability. In principal, it may also be considered to design the optical window to be made of glass.

The optical window is, for example, sealingly connected to the edge of an opening of the receptacle. The connection of the optical window to the receptacle is, for example, designed as one of the above disclosed connections of the sterile filter to the receptacle. According to one embodiment, the window is integrally configured with the receptacle, for example in that it consists of a plastic which is integrally connected to the plastic of the remaining receptacle. The receptacle with an integral optimal window is, for example, produced in a single or multi component injection-moulding method from one or more plastics.

According to one embodiment, the receptacle comprises devices for stacking at the bottom and top. This allows a space-saving arrangement. According to a further embodiment, the receptacle comprises complementary support surfaces and guide surfaces at the bottom and top for stacking a plurality of receptacles with identically configured bases and tops. On the support surfaces, the receptacles stacked one above the other rest on top of one another. The guide surfaces prevent the receptacles from falling down to the side from the stack.

According to one embodiment, the receptacle consists entirely or partially of a rigid material. According to a further embodiment, the receptacle is a substantially rigid container.

According to one embodiment, the receptacle consists entirely or partially of a flexible material. According to a further embodiment, the receptacle is a bag. A sterile filter configured as a porous membrane is, for example, integrated in a bag in which it forms a side wall of the bag, which is connected at the edge to at least one further side wall of the bag. For example, the bag consists of two side walls positioned on top of one another, which are welded on the two longitudinal sides and on one transverse side to one another and are not welded to one another on a further transverse side, so that they form at that point an opening. According to a further example, all side walls of the bag consist of the sterile filter material. According to a further example, the bag is a tubular bag with a single side wall, which is completely or partially designed as a porous membrane. The opening of a bag may be closed easily by tying up the bag at the opening and/or by welding up the bag at the edge of the opening by means of a suitable welding device. In particular, a bag which may be tied up is tubular, for example in the vicinity of the opening or in its entirety.

Mixed shapes are also possible, i.e. receptacles which are partially rigid and partially flexible, for example rigid receptacles with a flexible sterile filter and/or with an opening in a flexible (for example tubular) partial region.

According to one embodiment, the receptacle comprises a label and/or carries a marker. This allows the user to identify the cell culture, which prevents mixing up their own cell cultures or other cell cultures.

According to one embodiment, the receptacle is produced entirely or partially from at least one plastic. Preferably, the receptacle is produced from a plastic which may be autoclaved and tempered in a suitable range for cell cultures (for example 30° C. to 50° C.). The use of plastic which allows an observation of the cultures in the culture vessel by means of microscopes through a wall and/or an optical window of the receptacle is also advantageous.

According to one embodiment of the method, the receptacle is sterilised before filling with cells. This is expedient, for example, before the reuse of the receptacle, but is also considered for receptacles which are provided sterilised by the manufacturer, in order to eliminate contaminants in an entirely reliable manner.

According to one embodiment, cells are filled into the culture vessel contained in the receptacle and subsequently the receptacle is closed in a contamination-proof manner. This is, for example, the case when a culture vessel is integrated in the receptacle. It is, however, also possible firstly to insert the culture vessel in the receptacle and then to fill the cells into the culture vessel contained in the receptacle.

When the culture vessel has to be inserted into the receptacle, generally one embodiment of the method is expedient in which cells are filled into the culture vessel, the culture vessel is inserted with the introduced cells into the receptacle and subsequently the receptacle is closed in a contamination-proof manner.

According to one embodiment, culture conditions are created outside the receptacle and introduced into the receptacle. This is, for example, the case when a receptacle provided with a sterile filter is inserted into an incubator and when a receptacle provided with connections is attached to an external gassing device. This is also the case when the receptacle is placed on the tempering plate of a tempering device.

According to a further embodiment, a gas comprising culture conditions is filtered in a sterile manner and introduced into the receptacle. The gas comprising culture conditions has, for example, a specific $CO_2$, $O_2$, water vapour content and if required a specific temperature.

According to one embodiment, as a result of heat transmission between the receptacle and an external tempering device a specific temperature is generated in the receptacle.

According one embodiment, at least one medium is supplied to the cells under culture conditions and/or at least one sample is removed.

According to one embodiment, the cells are observed in the receptacle under culture conditions. The observation preferably takes place through an optical window by means of a microscope.

According to one embodiment, an atmosphere preventing the evaporation of culture medium is established in the receptacle by evaporating a liquid. In this embodiment, culture conditions are directly created in the interior of the receptacle. The liquid is, for example, sterile water.

According to one embodiment, the culture vessel is removed from the receptacle, the cell culture is subjected to a control and subsequently the culture vessel is inserted into the same receptacle or into a new receptacle, the receptacle is closed in a contamination-proof manner and culture conditions are created for the cells in the receptacle.

According to one embodiment preventing mixing up, the receptacle is labelled and/or provided with a marker.

Finally, according to one embodiment the receptacle is discarded after the incubation is completed, i.e. disposed of. This simplifies the handling. The sterilising of the receptacle which is required for reuse, is dispensed with.

The invention is explained hereinafter with reference to the accompanying drawings which show, roughly schematically, different embodiments.

BRIEF DESCRIPTION OF THE SEVERAL VIEWS OF THE DRAWINGS

FIG. 1 shows a first embodiment of a device for the incubation of cells;

FIG. 2 shows a second embodiment of a device for the incubation of cells;

FIG. 3 shows a third embodiment of a device for the incubation of cells;

FIG. 4 shows a fourth embodiment of a device for the incubation of cells;

FIG. 5 shows a fifth embodiment of a device for the incubation of cells;

FIG. 6 shows several receptacles on a temperating plate;

FIG. 7 shows a plurality of the receptacles of the fourth and fifth embodiments stacked on top of one another, and FIG. 8 shows an incubator with conventional cell culture vessels 2.2 together with the receptacles of the fourth embodiment.

In the following description of the different embodiments, elements of the device having the same designation are denoted by the same reference numerals, different embodiments being provided by a point placed thereafter and an individual number placed thereafter.

DETAILED DESCRIPTION OF THE INVENTION

While this invention may be embodied in many different forms, there are described in detail herein a specific preferred embodiment of the invention. This description is an exemplification of the principles of the invention and is not intended to limit the invention to the particular embodiment illustrated.

A substantially box-shaped receptacle 1.1 (see FIG. 1) has an integrated culture vessel 2.1, which is fixedly connected to a base 3.1 of the receptacle 1.1. The flat base 3.1 may be positioned on a tempering plate 4 of a tempering device 5.

In a top wall 6.1 the receptacle 1.1 has a closable opening 7.1 for introducing and removing cells, culture medium etc. The opening 7.1 is configured to be relatively small, as only the aforementioned media have to be passed through. Optionally, before closing the opening 7.1 an atmosphere creating cell culture conditions is introduced into the receptacle 1.1. This may also be repeated.

Moreover, a receptacle 1.2 (see FIG. 2) is shown which in the top wall 6.2 has a larger closable opening 7.2 through which a culture vessel 2.2 with a lid 8 may be inserted and removed. Moreover, the dimensions of the receptacle 1.2 are matched to the size of the insertable culture vessel 2.2 with the lid 8. The flat base 3.1 is, in turn, able to be positioned on the tempering plate 4 of a tempering device 5.

The receptacle 1.3 (see FIG. 3) differs from that disclosed above in that it is dimensioned such that a plurality of culture vessels 2.2. with lids 8 stacked on top of one another fit inside said receptacle. Moreover, the opening 7.3 in the top wall 6.3 is designed to be larger so that a plurality of culture vessels 2.2 with lids 8 stacked on top of one another pass through. Optionally, an atmosphere creating cell culture conditions is introduced into the receptacle 1.3 through the opening 7.3 before closing the opening 7.3. This may also be repeated.

The receptacle 1.4 (see FIG. 4) has a sterile filter 9 in one wall 7.1, in contrast to the receptacle 1.2. Moreover, it has an optical window 10 integrated in the top wall 6.4 for observing the cells in the culture vessel 2.2 by means of a microscope. Additionally or instead of the optical window 10 an optical window 10.1 is integrated in a base 3.1 of the receptacle 1.4 which allows observation of the cells in the culture vessel 2.2 by means of an inverted microscope.

The receptacle 1.4 is able to be incubated together with conventional cell culture vessels 2.2 in an incubator 11 (see FIG. 8). The atmosphere fed into the incubator 11 through a gas connector 12 penetrates through the sterile filter 9 into the inside of the receptacle 1.4 and as far as the cells in the culture vessel 2.2.

In contrast to the receptacle 1.4, the receptacle 1.5 (see FIG. 5) comprises in one wall 7.2 a connector 13 with a through-passage to the inside of the receptacle 1.5 and a valve 14 incorporated in the connection for opening and closing the through-passage. The connection 13 may be attached to an external gassing device.

A plurality of receptacles 1.5 are, for example, able to be positioned on the tempering plate 4 of a tempering device 5 (see FIG. 6), at the same time treatment with gas being carried out via the connections 13 by means of an external gassing device, not shown. This is also shown in the drawings.

Moreover, the drawings show the capacity of the receptacles 1.4 and receptacles 1.5 to be freely combined (see FIG. 7), which may be put into an incubator 11 together, stacked on top of one another, the receptacles 1.5 being able to be attached to an external gassing device in order to generate therein a specific atmosphere.

The invention claimed is:

1. Device for the incubation of cells comprising a sterile or sterilisable, portable receptacle (1) for enclosing in a contamination-proof manner at least one insertable culture vessel (2) for accommodating cells with at least one closable opening (7) for introducing and/or removing a culture vessel (2) and optionally cells and/or culture medium into and/or from the receptacle (1) and at least one device for creating culture conditions (11) in the receptacle, which comprises at least one sterile filter (9) in at least one wall (7.1) of the receptacle (1.4).

2. Device according to claim 1 comprising a plurality of culture vessels (2.1, 2.2).

3. Device according to claim 2 comprising devices for the releasable connection of at least one culture vessel (2) to the receptacle (1).

4. Device according to claim 1 comprising a culture vessel (2.1) integrated in the receptacle (1.1).

5. Device according to claim 4, comprising at least one culture vessel (2.1) connected fixedly and inseparably to the receptacle (1.1).

6. Device according to claim 1, comprising a receptacle (1) suitable for enclosing and/or inserting and/or removing at least one multiwell culture plate.

7. Device according to claim 1, comprising a receptacle (1) suitable for enclosing and/or inserting and/or removing at least one culture flask.

8. Device according to claim 1 comprising a receptacle (1) suitable for enclosing and/or inserting and/or removing at least one culture dish.

9. Device according to claim 1, in which the device for creating culture conditions comprises an incubator (11) with integral tempering device and gassing device for accommodating at least one receptacle (1.4).

10. Device according to claim 1, in which the device for creating culture conditions comprises at least one connection (14) of the receptacle (1.5) with a through-passage traversing a wall of the receptacle for attaching the receptacle (1.5) to at least one gassing device.

11. Device according to claim 10, in which the device for creating culture conditions comprises a gassing device and at least one tube via which the gassing device is connected or may be connected to at least one connection (13).

12. Device according to claim 10, in which the connection (13) comprises a valve (14) for opening and closing the through-passage.

13. Device according to claim 1, in which the receptacle (1.1) comprises a planar base (3.1) for positioning on a tempering plate (4) of a tempering device (5).

14. Device according to claim 1, in which the device for creating culture conditions comprises at least one open vessel which is integrated in the receptacle (1) and/or which may be inserted into the receptacle (1) for evaporating a liquid introduced into the vessel.

15. Device according to claim 1, in which the device for creating culture conditions comprises a mixing device on which the receptacle is arranged or may be arranged in order to subject the receptacle (1) to a mixing motion.

16. Device according to claim 1, in which at least one opening (7) of the receptacle (1) is reclosable.

17. Device according to claim 1, in which the receptacle (1.4) comprises at least one optical window (10) for observing the cells in the culture vessel (2.2).

18. Device according to claim 1, in which the receptacle (1) comprises devices for stacking at the bottom and top.

19. Device according to claim 18, in which the receptacle (1) comprises complementary support surfaces and guide surfaces at the bottom and top for stacking a plurality of receptacles (1) with identically configured bases and tops.

20. Device according to claim 1, in which the receptacle (1) consists entirely or partially of a rigid material.

21. Device according to claim 20, in which the receptacle (1) is a substantially rigid container.

22. Device according to claim 1, in which the receptacle (1) consists entirely or partially of a flexible material.

23. Device according to claim 22, in which the receptacle (1) is a bag.

24. Device according to claim 1, in which the receptacle (1) comprises a label and/or carries a marker.

25. Device according to claim 1, in which the receptacle (1) is produced entirely or partially from at least one plastic.

26. Device according to claim 1, in which the receptacle (1) and/or the cell culture vessel (2) is/are a single-use item.

27. Method for the incubation of cells, comprising the steps of:
providing a device for the incubation of cells comprising a sterile or sterilisable, portable receptacle (1) for enclosing in a contamination-proof manner at least one insertable culture vessel (2) for accommodating cells with at least one closable opening (7) for introducing and/or removing a culture vessel (2) and optionally cells and/or culture medium into and/or from the receptacle (1) and at least one device for creating culture conditions (11) in the receptacle, which comprises at least one sterile filter (9) in at least one wall (7.1) of the receptacle (1.4)
in which at least one culture vessel (2) containing cells is provided enclosed by a sterile, portable receptacle (1) in a contamination-proof manner and culture conditions are created for the cells in the receptacle (1), in which a gas comprising culture conditions is filtered in a sterile manner and introduced into the receptacle (1).

28. Method according to claim 27, in which the receptacle (1) is sterilised before filling with cells.

29. Method according to claim 27, in which cells are filled into the culture vessel (2) contained in the receptacle (1) and subsequently the receptacle (1) is closed in a contamination-proof manner.

30. Method according to claim 29, in which cells are filled into the culture vessel (2), the culture vessel (2) is inserted with the introduced cells into the receptacle (1) and subsequently the receptacle (1) is closed in a contamination-proof manner.

31. Method according to claim 27, in which culture conditions are created outside the receptacle (1) and introduced into the receptacle (1).

32. Method according to claim 27, in which as a result of heat transmission between the receptacle (1) and an external tempering device (5) a specific temperature is generated in the receptacle (1).

33. Method according to claim 27, in which at least one medium is supplied to the cells under culture conditions and/or at least one sample is removed.

34. Method according to claim 27, in which the cells are observed in the receptacle (1) under culture conditions.

35. Method according to claim 27, in which an atmosphere preventing the evaporation of culture medium is established in the receptacle (1) by evaporating a liquid.

36. Method according to claim 27, in which the culture vessel (2) is removed from the receptacle (1), the cell culture subjected to a control and subsequently the culture vessel (2) is inserted into the same receptacle or into a new receptacle (1), the receptacle (1) is closed in a contamination-proof manner and culture conditions are created for the cells in the receptacle (1).

37. Method according to claim 27, in which the receptacle (1) is labelled and/or provided with a marker.

38. Method according to claim 27, in which the receptacle (1) is discarded after the incubation is completed.

* * * * *